United States Patent
Sanchez et al.

[11] Patent Number: 5,866,712
[45] Date of Patent: Feb. 2, 1999

[54] OXALIC ACID PEROXIDE COMPOSITIONS AND USES

[75] Inventors: Jose Sanchez, Grand Island, N.Y.; Daryl L. Stein, West Chester, Ohio

[73] Assignee: ELF Atochem North America, Inc., Philadelphia, Pa.

[21] Appl. No.: 948,363

[22] Filed: Oct. 10, 1997

Related U.S. Application Data

[60] Provisional application No. 60/034,526 Dec. 30, 1996.
[51] Int. Cl.$^6$ .................................................. C07C 229/00
[52] U.S. Cl. ......................... 560/170; 560/190; 560/174; 526/216; 526/232.5; 526/227; 526/232; 525/447
[58] Field of Search ................................ 526/216, 232.5, 526/227, 232; 525/447; 560/174, 190, 170

[56] References Cited

U.S. PATENT DOCUMENTS

| | | | |
|---|---|---|---|
| 3,236,872 | 2/1966 | Manly et al. | 260/153 |
| 3,660,468 | 5/1972 | McKellin | 260/488 |
| 3,671,651 | 6/1972 | D'Angelo | 260/463 |
| 3,706,818 | 12/1972 | Mageli et al. | 260/885 |
| 3,725,455 | 4/1973 | D'Angelo et al. | 260/463 |
| 3,839,390 | 10/1974 | D'Angelo et al. | 260/453 |
| 3,846,396 | 11/1974 | D'Angelo et al. | 260/94.9 |
| 3,853,957 | 12/1974 | D'Angelo et al. | 260/476 |
| 4,525,308 | 6/1985 | Sanchez | 260/453 |
| 4,634,753 | 1/1987 | Sanchez | 526/216 |
| 5,475,072 | 12/1995 | Sanchez et al. | 526/266 |

*Primary Examiner*—Samuel Barts
*Attorney, Agent, or Firm*—Stanley A. Marcus; Royal E. Bright

[57] ABSTRACT

A novel peroxide composition of Structure A,

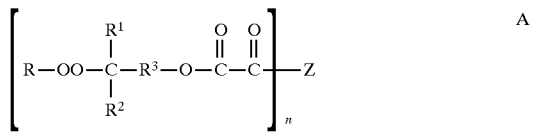

and use of the novel oxalic acid peroxide composition of Structure A as an initiator; a) for curing of unsaturated polyester resins, b) for polymerizing ethylenically unsaturated monomers, c) for crosslinking of polyolefins, d) for curing of elastomers, e) for modifying polyolefins, f) for grafting of vinyl monomers onto polymer backbones and g) for compatibilizing blends of two or more incompatible polymers are disclosed.

9 Claims, No Drawings

OXALIC ACID PEROXIDE COMPOSITIONS AND USES

This Application claims priority from Provisional Application Ser. No. 60/034,526, filed Dec. 30, 1996.

BACKGROUND OF THE INVENTION a) Field of the Invention

This invention relates to new and novel compositions of matter classified in the art of chemistry as oxalic acid peroxide compositions of Structure A,

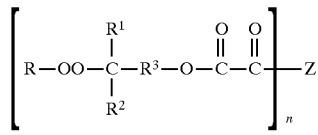

[The definitions of R, $R^1$, $R^2$, $R^3$, Z, and n are given in the SUMMARY OF THE INVENTION]
e.g., allyl 3-t-butylperoxy-1,3-dimethylbutyl oxalate, and use of the novel oxalic acid peroxide compositions of Structure A. The compositions possess inherent applied use characteristics making them suitable for use as initiators a) for polymerizing ethylenically unsaturated monomers, b) for curing of unsaturated polyester resins, c) for curing of elastomers, d) for crosslinking of polyolefins, e) for modifying polyolefins, f) for grafting of vinyl monomers onto polymer backbones and g) for compatibilizing blends of two or more incompatible polymers.

There is a need in the polymer industry for efficient, free-radical crosslinking agents for olefin polymers which give longer scorch times and yet result in faster crosslinking rates. Because of its low melt flow high density polyethylene (HDPE) must be compounded with peroxides at temperatures where the scorch time is relatively short. If the scorch time is too short, premature crosslinking of HDPE occurs during the peroxide compounding step. This is highly undesirable. In the crosslinking of HDPE the peroxide that is predominantly used for crosslinking is 2,5-dimethyl-2,5-di (t-butylperoxy)-3-hexyne (Lupersol 130; manufactured by ELF ATOCHEM North America, Inc.). Of all the commercial organic peroxides, Lupersol 130 has the highest 10 hour half-life temperature (131° C.). The 10 hour half-life temperature of an initiator is defined as the temperature at which 50% of the initiator will decompose in 10 hours. Generally, the higher the 10 hour half-life temperature the longer the scorch time at a given temperature.

Although Lupersol 130 gives adequate scorch times when compounded into HDPE, polymer producers complain of the noxious decomposition products that Lupersol 130 produces during crosslinking of polyethylene. The noxious decomposition products are thought to be derived from the carbon-carbon triple bond in Lupersol 130 since a similar peroxide that lacks the carbon-carbon triple bond, 2,5-dimethyl-2,5-di(t-butylperoxy)hexane, does not produce noxious decomposition products. An efficient polyethylene crosslinking agent which yields lengthened scorch times and produces less noxious decomposition products is needed by the polyethylene crosslinking industry.

A novel oxalic acid peroxide composition of the instant invention, allyl 3-t-butylperoxy-1,3-dimethylbutyl oxalate, satisfied most of these crosslinking criteria and was found to be a more effective HDPE crosslinking agent than was Lupersol 130. At 385° F. in HDPE, allyl 3-t-butylperoxy-1, 3-dimethylbutyl oxalate was found to be significantly more efficient than Lupersol 130 on an equivalent basis and was found to crosslink HDPE much more rapidly than Lupersol 130. Hence, it was superior to Lupersol 130 for crosslinking of HDPE. Because allyl 3-t-butylperoxy-1,3-dimethylbutyl oxalate contains no carbon-carbon triple bond, generation of noxious decomposition products during crosslinking of polyethylene is unlikely.

In recent years most of the new polymeric materials that have been commercialized are polymeric blends and alloys composed of two or more different polymers. The reasons for this trend to commercial development of polymer blends and alloys include the short time required for development and commercialization of these materials, the relatively low cost involved in carrying out the R&D effort needed to develop these materials compared to development of entirely new polymers from monomers, and the ability to develop polymeric blends and alloys that are "tailor made" to meet end use property specifications, hence, they are neither over-engineered nor under-engineered, but just right.

The polymer property improvements achieved by blending include:

Better processability

Impact strength enhancement

Improved flame retardance

Improved barrier properties

Improved tensile properties

Improved adhesion

Improved melt flow

Enhanced heat distortion temperature (HDT)

Enhanced heat resistance

Improved stiffness

Improved chemical resistance

Improved ultraviolet light stability

The major problem encountered in developing new blends and alloys is the inherent incompatibility or immiscibility of almost all mixtures of two or more polymers. The consequence of incompatibility of polymeric blends and alloys is that they are unstable and, with sufficient time and temperature, form separate phases, thus physical properties of the polymeric blends and alloys suffer. Generally, resin compounders have found that block and graft copolymers having polymeric segments that are compatible with the individual polymer components of blends and alloys enable formation of blends and alloys having enhanced phase stabilities and physical properties.

Low cost blends and alloys are commercially produced from two or more addition polymers such as blends involving low density polyethylene (LDPE), linear low density polyethylene (LLDPE), high density polyethylene (HDPE) and polypropylene (PP). The compatibility of these low cost blends can be improved by crosslinking with peroxides or by use of compatibilizing block or graft copolymers as mentioned above.

An important use of peroxides such as the novel oxalic acid peroxide compositions of Structure A is their utility in preparing graft copolymers useful for compatibilizing polymeric blends and alloys. The novel oxalic acid peroxide compositions of Structure A of the instant invention, are effective in the preparation of graft copolymer compositions. Such graft copolymers have utility in compatibilizing polymer blends and alloys.

b) Description of the Prior Art

U.S. Pat. No. 3,236,872 (Feb. 22, 1966, to Laporte Chemical, Ltd.) discloses hydroxy-peroxides of the structure:

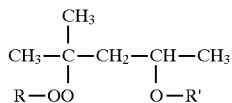

(wherein R— is a H—, an acyl, an aroyl or alkyl group, especially the t-butyl group, t-amyl or the hexylene glycol residue; R'— is an H— or an acyl, aroyl or alkyl group.)

U.S. Pat. No. 4,525,308 (Jun. 25, 1985, to Pennwalt Corp.) and U.S. Pat. No. 4,634,753 (Jan. 6, 1987, to Pennwalt Corp.) disclose hydroxy-peroxyesters (above structure where R'— is H— and R— is an acyl group) having 10 hour half-life temperatures below about 75° C.

U.S. Pat. No. 3,853,957 (Dec. 10, 1974, to Pennwalt Corp.) discloses diperoxyketals and ketone peroxides containing hydroxy and acyloxy groups.

U.S. Pat. No. 3,846,396 (Nov. 5, 1974, to Pennwalt Corp.) and U.S. Pat. No. 3,725,455 (Apr. 3, 1973, to Pennwalt Corp.) disclose coupled peroxides of the structure,

R—W—R' where R— and R'— are identical and are peroxide containing alkoxy radicals having at least two carbons and an oxygen atom between the peroxide groups (—OO—) of the R— and R'— groups and —W— is a diradical selected from the class consisting of several diradical structures including,

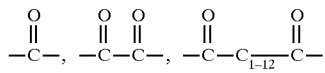

U.S. Pat. No. 3,846,396 and U.S. Pat. No. 3,725,455 are close art when —W— is —C(O)—C(O)—. However, the structures of this art do not anticipate the compositions of Structure A.

U.S. Pat. No. 3,706,818 (Dec. 19, 1972, to Pennwalt Corp.) and U.S. Pat. No. 3,839,390 (Oct. 1, 1974, to Pennwalt Corp.) disclose sequential polyperoxides possessing peroxide moieties of differing structures and activities in the same molecule. The structures of this art do not anticipate the sequential polyperoxides of Structure A.

U.S. Pat. No. 3,671,651 (Jun. 20, 1972, to Pennwalt Corp.) discloses peroxy compounds containing haloformate (e.g., chloroformate and carbonyl chloride) groups. Some of the novel oxalic acid peroxide compositions of Structure A contain the chlorooxalate group, —O—C(O)—C(O)—Cl, which is different, easier to incorporate onto a hydroxy-peroxy compound than is a haloformate group (especially when the hydroxyl group is a secondary or a tertiary hydroxyl group) and which is more reactive in subsequent reactions than a haloformate (i.e., with a secondary or a tertiary hydroxyl compound and/or in the absence of a base). Hence, the novel oxalic acid peroxide compositions of Structure A advance the art over that disclosed in U.S. Pat. No. 3,671,651.

U.S. Pat. No. 3,660,468 (May 2, 1972, to Pennwalt Corp.) discloses peroxyester compounds containing carboxy groups. The carboxy compounds of Structure A contain the —O—C(O)—C(O)—OH group which is significantly different than the carboxy group of the carboxy-containing peroxyesters of U.S. Pat. No. 3,660,468. In addition, the carboxy compositions of Structure A are more easily produced than are the carboxy-containing peroxyesters of U.S. Pat. No. 3,660,468.

c) Definitions

In the instant invention, t-cycloalkyl refers to the monoradical structure,

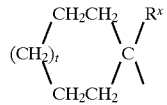

where t is 0 to 2 and $R^x$ is a lower alkyl radical of 1 to 4 carbons, t-alkynyl is the monoradical structure,

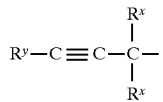

where $R^y$ is hydrogen or a lower alkyl radical of 1 to 4 carbons, and t-aralkyl is the monoradical structure,

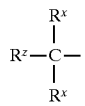

where $R^z$ is an aryl radical of 6 to 10 carbons.

When any generalized functional group or index, such as R, $R^1$, $R^2$, x, n, etc., appears more than once in a general formula or structure, the meaning of each is independent of one another.

SUMMARY OF THE INVENTION

The invention provides in a composition aspect, a novel oxalic acid peroxide composition of Structure A:

$$\left[ R-OO-\underset{\underset{R^2}{|}}{\overset{\overset{R^1}{|}}{C}}-R^3-O-\overset{O}{\overset{\|}{C}}-\overset{O}{\overset{\|}{C}}\right]_n Z \qquad A$$

where n is 1 or 2, and R is selected from the group consisting of a t-alkyl radical of 4 to 12 carbons, a t-cycloalkyl radical of 6 to 13 carbons, a t-alkynyl radical of 5 to 9 carbons, a t-aralkyl radical of 9 to 13 carbons and the structures (a), (b), (c), (d) and (e),

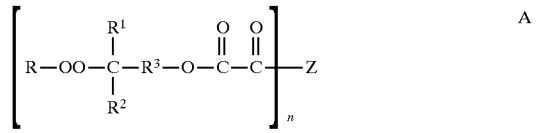

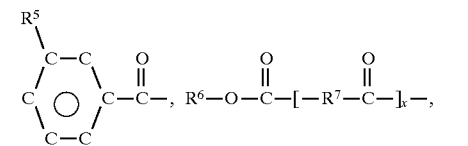

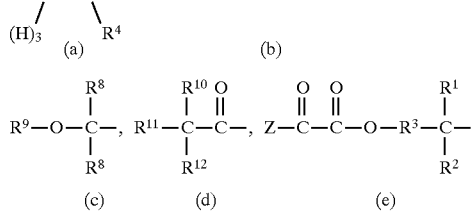

where $R^4$ and $R^5$ are the same or different and are selected from the group consisting of hydrogen, lower alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, hydroxy, fluoro, chloro or bromo, and, x is 0 or 1, $R^6$ is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6 to 10 carbons, hydroxy, chloro, bromo or cyano, and a substituted or unsubstituted cycloalkyl radical of 5 to 12 carbons optionally having an oxygen atom or a nitrogen atom in the cycloalkane ring, with substituents being one or more lower alkyl radicals of 1 to 4 carbons, and, $R^7$ is selected from a substituted or unsubstituted alkylene diradical of 2 to 3 carbons, substituents being one or more lower alkyl radicals of 1 to 4 carbons, and substituted or unsubstituted 1,2-, 1,3- and 1,4-phenylene diradicals, substituents being one or more lower alkyl radicals of 1 to 4 carbons, chloro, bromo, nitro or carboxy, and, $R^8$ is a lower alkyl radical of 1 to 4 carbons, and, additionally, the two $R^8$ radicals may be concatenated to form an alkylene diradical of 4 to 5 carbons, and, $R^9$ is a lower alkyl radical of 1 to 4 carbons, and, $R^{10}$, $R^{11}$, and $R^{12}$ can be the same or different and are selected from the group consisting of hydrogen, alkyl radicals of 1 to 8 carbons, aryl radicals of 6 to 10 carbons, alkoxy radicals of 1 to 8 carbons and aryloxy radicals of 6 to 10 carbons, and, $R^1$ and $R^2$ are lower alkyl radicals of 1 to 4 carbons, and, when R is selected from a t-alkyl radical of 4 to 12 carbons $R^2$ can additionally be a t-alkylperoxy radical of 4 to 12 carbons, $R^3$ is selected from the group consisting of a substituted or unsubstituted alkylene diradical of 2 to 4 carbons and a substituted or unsubstituted alkynylene diradical of 2 to 4 carbons, substituents being one or more lower alkyl radicals of 1 to 4 carbons, and, when n is 1, Z is selected from the group consisting of $OR^{13}$, $NR^{13}R^{14}$, OO—R, Cl and Br, where $R^{13}$ and $R^{14}$ are the same or different and are selected from the group consisting of hydrogen, substituted or unsubstituted alkyl radicals of 1 to 18 carbons, substituents being one or more alkyl radicals of 1 to 6 carbons, alkoxy radicals of 1 to 6 carbons, aryloxy radicals of 6 to 10 carbons, acryoyloxy radicals, methacryloyloxy radicals, chloro, bromo and cyano, substituted or unsubstituted alkenyl radicals of 3 to 12 carbons, substituents being one or more lower alkyl radicals of 1 to 4 carbons, substituted or unsubstituted aryl radicals of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, substituted or unsubstituted aralkyl radicals of 7 to 11 carbons, substituents being one or more alkyl radicals of 1 to 6 carbons, alkoxy radicals of 1 to 6 carbons, aryloxy radicals of 6 to 10 carbons, chloro, bromo and cyano, and substituted or unsubstituted cycloalkyl radicals of 5 to 12 carbons optionally having an oxygen atom or a nitrogen atom in the cycloalkane ring, with substituents being one or more lower alkyl radicals of 1 to 4 carbons, and Z is also selected from structure (g),

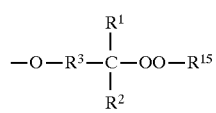
(g)

$R^{15}$ is selected from the definitions of R, with the proviso that R and $R^{15}$ are not the same, and when n is 2, Z is selected from the group consisting of structures (h), (i), and (j),

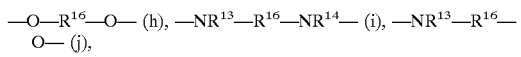

$R^{16}$ is selected from the group consisting of substituted or unsubstituted alkylene diradicals of 2 to 10 carbons, substituents being one or more lower alkyl radicals of 1 to 4 carbons, and arylene diradicals of 6 to 14 carbons, substituents being one or more lower alkyl radicals of 1 to 4 carbons.

B. The invention provides in a process aspect a process for use of the oxalic acid peroxide compositions of Structure A as free-radical initiators, in effective initiating amounts, for the initiation of free-radical reactions selected from the group consisting of:

a. curing of unsaturated polyester resin compositions, b. polymerizing ethylenically unsaturated monomers (such as styrene, ethylene) compositions, c. crosslinking of olefin thermoplastic polymer compositions, d. curing of elastomer compositions, e. modifying polyolefin compositions, f. grafting of ethylenically unsaturated monomer substrates onto olefin homo- and copolymer substrates, and, g. compatibilizing blends of two or more normally incompatible polymer substrates;

which comprises heating said substrates in the presence of an effective initiating amount of one or more peroxides as defined in A. above, for a time sufficient to at least partially decompose said peroxide, to perform the free-radical reaction.

DETAILED DESCRIPTION

Novel Oxalic Acid Peroxide Compositions of Structure A—Preparative Methods

The novel oxalic acid peroxide compositions of Structure A can be prepared by several methods.

One method involves reacting a hydroxy-peroxide of Structure Y with an oxalyl halide of Structure X in the presence of an optional base and an optional solvent to form a novel composition of Structure A:

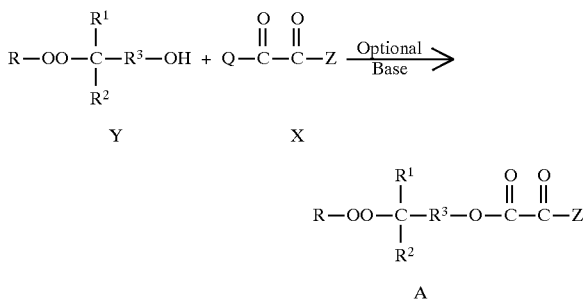

[R is as previously defined and Q=Br or Cl]

Hydroxy-peroxides of Structure Y, where R=t-alkyl, t-cycloalkyl, t-alkynyl, t-aralkyl and HO—$R^3$—C($R^1$)($R^2$)—, are known in the art (U.S. Pat. No. 3,236,872).

Hydroxy-peroxides of Structure Y, where R=structure (a), can be prepared by reacting a substituted or unsubstituted benzoyl halide of Structure W with a hydroxy-hydroperoxide of Structure V in the presence of a base and an optional solvent:

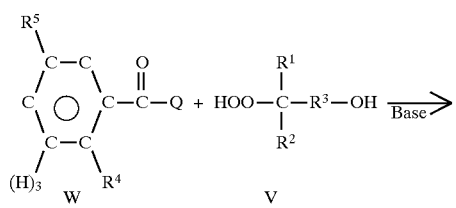

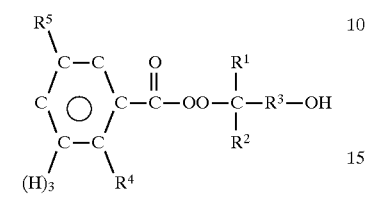

Hydroxy-peroxides of Structure Y, where R=structure (b) and x=0, can be prepared by reacting alkyl haloformates of Structure U with a hydroxy-hydroperoxide of Structure V in the presence of a base and an optional solvent:

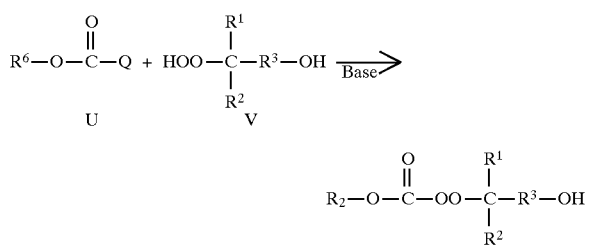

Hydroxy-peroxides of Structure Y, where R=structure (b) and x=1, can be prepared by reacting an ester carboxylic acid halide of Structure T with a hydroxy-hydroperoxide of Structure V in the presence of a base and an optional solvent:

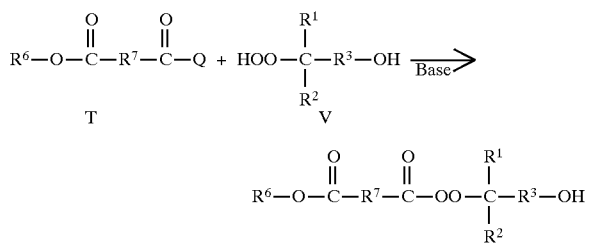

Hydroxy-peroxides of Structure Y, where R=structure (c), can be prepared by reacting an unsaturated ether of Structure S with a hydroxy-hydroperoxide of Structure V in the presence of an optional acid and an optional solvent:

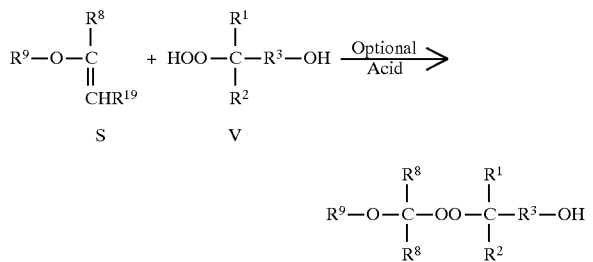

[Where $R^{19}$ contains one less methylene diradical than $R^8$]

Some hydroxy-peroxides of Structure Y, where R is structure (d) are known in the art (U.S. Pat. No. 4,525,308). This class of hydroxy-peroxides can be synthesized by reacting hydroperoxides of structure V with carboxylic acid halides or anhydrides of stucture P in the presence of an optional base and an optional solvent:

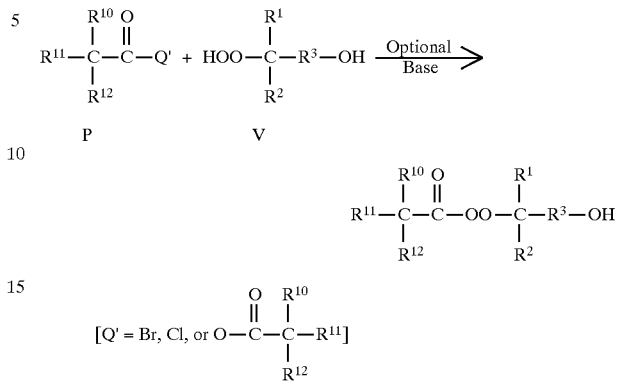

Non-limiting examples of suitable optional inorganic bases that are useful in the synthetic processes of this invention include sodium hydroxide, sodium carbonate, sodium hydrogen carbonate, potassium hydroxide, potassium carbonate, potassium hydrogen carbonate, calcium hydroxide, barium hydroxide, magnesium hydroxide, calcium carbonate and trisodium phosphate. Non-limiting examples of suitable optional organic bases useful for preparing the peroxide compositions of this invention include trimethylamine, triethylamine, tributylamine, 1,4-diazabicyclo[2.2.2]octane, pyridine, N,N-dimethylaniline, N,N-diethylaniline, p-N,N-dimethylaminopyridine, tetramethylurea and methylpyridines.

Non-limiting examples of suitable optional solvents include pentane, hexanes, heptanes, dodecanes, odorless mineral spirits mixtures, toluene, xylenes, cumene, methylene chloride, ethyl acetate, 2-ethylhexyl acetate, isobutyl isobutyrate, dimethyl adipate, dimethyl succinate, dimethyl glutarate (or mixtures thereof), dimethyl phthalate, dibutyl phthalate, benzyl butyl phthalate, diethyl ether, methyl t-butyl ether, 2-methoxyethyl acetate and others.

Non-limiting examples of suitable optional acids that are useful in the synthetic processes of this invention include hydrochloric acid, perchloric acid, phosphoric acid, sulfuric acid, sodium hydrogen sulfate, potassium hydrogen sulfate, acetic acid, trifluoroacetic acid, methanesulfonic acid and benzenesulfonic acid.

Non-limiting examples of suitable hydroxy-hydroperoxides of Structure V include 3-hydroxy-1,1-dimethylpropyl hydroperoxide, 3-hydroxy-1,1-dimethylbutyl hydroperoxide and 4-hydroxy-1,1-dimethylbutyl hydroperoxide.

Non-limiting examples of suitable acid halides of Structure W include benzoyl chloride, 2-methylbenzoyl chloride, 2-ethylbenzoyl chloride, 2-methoxybenzoyl chloride, 2,6-dimethylbenzoyl chloride, 2-phenylbenzoyl chloride, 2-chlorobenzoyl chloride, 2,4-dichlorobenzoyl chloride, 2-bromobenzoyl chloride, 2-bromobenzoyl bromide, 2-fluorobenzoyl chloride, 2-acetoxybenzoyl chloride, and 2-(t-butylperoxycarbonyl)benzoyl chloride.

Non-limiting examples of suitable carboxylic acid halides and anhydrides of Structure P include pivaloyl chloride, neoheptanoyl chloride, neodecanoyl chloride, neotridecanoyl chloride, 2-ethylbutyryl chloride, 2-ethylhexanoyl chloride, isobutyryl chloride, cyclohexane carboxylic acid chloride, acetic anhydride, propionic anhydride, and isobutyric anhydride Non-limiting examples of suitable of alkyl haloformates of Structure U include methyl chloroformate, ethyl chloroformate, isopropyl chloroformate, isopropyl bromoformate, butyl chloroformate, 2-butyl chloroformate, neopentyl chloroformate, 2-ethylhexyl chloroformate, 2-ethylbutyl chloroformate, 2-butyloctyl chloroformate, 4-methyl-2-pentyl chloroformate, dodecyl chloroformate, hexadecyl chloroformate, 2-chloroethyl chloroformate, 2-butoxyethyl chloroformate, 2-phenoxyethyl chloroformate, cyclohexyl chloroformate, 4-t-butylcyclohexyl chloroformate, 3,3,5-trimethylcyclohexyl chloroformate, cyclododecyl chloroformate, 2,2,6,6-tetramethyl-4-piperidinyl chloroformate (and hydrochloride salt) and 1,2,2,6,6-pentamethyl-4-piperidinyl chloroformate (and hydrochloride salt). The alkyl haloformates of Structure U can be prepared by reacting the corresponding alcohols with excess phosgene.

Non-limiting examples of suitable acid halides of Structure T include 2-methoxycarbonylbenzoyl chloride, 2-n-butoxycarbonylbenzoyl chloride, 2-(2-ethylhexoxycarbonyl)benzoyl chloride, 2-cyclohexoxycarbonyl-benzoyl chloride, 3-ethoxycarbonylpropionyl chloride, 4-(n-butoxycarbonyl)butyryl chloride and 3,4,5,6-tetrachloro-2-methoxycarbonylbenzoyl chloride.

The acid halides of Structures W, T, and P can be prepared by treating the corresponding carboxylic acids with acid halogenating agents such as $PCl_3$, $POCl_5$, $PCl_5$, thionyl chloride, thionyl bromide, phosgene (in the presence of catalysts such as dimethylforamide, DMF), benzotrichloride and others.

Non-limiting examples of suitable unsaturated ethers of Structure S include methyl isopropenyl ether, ethyl isopropenyl ether, n-butyl isopropenyl ether, 1-methoxy-1-cyclohexene, 1-ethoxy-1-cyclohexene and 1-methoxy-3,3,5-trimethylcyclohexene.

Non-limiting examples of suitable hydroxyperoxides of Structure Y, where R=structure (a), useful for preparing the novel oxalic acid peroxide compositions of Structure A, include 3-hydroxy-1,1-dimethylpropyl peroxy-(2-chlorobenzoate), 3-hydroxy-1,1-dimethylbutyl peroxybenzoate, 3-hydroxy-1,1-dimethylbutyl peroxy-(2-methylbenzoate), 3-hydroxy-1,1-dimethylbutyl peroxy-(2,4-dimethylbenzoate), 3-hydroxy-1,1-dimethylbutyl peroxy-(2,6-dimethylbenzoate), 3-hydroxy-1,1-dimethylbutyl peroxy-(2-fluorobenzoate), 3-hydroxy-1,1-dimethylbutyl peroxy-(2-chlorobenzoate), 3-hydroxy-1,1-dimethylbutyl peroxy-(2-bromobenzoate), 3-hydroxy-1,1-dimethylbutyl peroxy-(2,4-dichlorobenzoate), 3-hydroxy-1,1-dimethylbutyl peroxy-(2-phenylbenzoate), 3-hydroxy-1,1-dimethylbutyl peroxy(2-methoxybenzoate) and 3-hydroxy-1,1-dimethylbutyl peroxy(2-acetoxybenzoate).

Non-limiting examples of suitable hydroxyperoxides of Structure Y, where R=structure (b) and x=0, useful for preparing the novel oxalic acid peroxide compositions of Structure A, include OO-(3-hydroxy-1,1-dimethylpropyl) O-(2-ethylhexyl) monoperoxycarbonate, OO-(3-hydroxy-1,1-dimethylbutyl) O-isopropyl monoperoxycarbonate, OO-(3-hydroxy-1,1-dimethylbutyl) O-(2-butyl) monoperoxycarbonate, OO-(3-hydroxy-1,1-dimethylbutyl) O-(2-ethylhexyl) monoperoxycarbonate, OO-(3-hydroxy-1,1-dimethylbutyl) O-(2-butyloctyl) monoperoxycarbonate, OO-(3-hydroxy-1,1-dimethylbutyl) O-cyclohexyl monoperoxycarbonate, OO-(3-hydroxy-1,1-dimethylbutyl) O-cyclododecyl) monoperoxycarbonate, OO-(3-hydroxy-1,1-dimethylbutyl) O-(4-t-butylcyclohexyl) monoperoxycarbonate, OO-(3-hydroxy-1,1-dimethylbutyl) O-(2,2,6,6-tetramethyl-4-piperidinyl) monoperoxycarbonate (and salts) and OO-(3-hydroxy-1,1-dimethylbutyl) O-(1,2,2,6,6-pentamethyl-4-piperidinyl) monoperoxycarbonate (and salts).

Non-limiting examples of suitable hydroxyperoxides of Structure Y, where R=structure (b) and x=1, useful for preparing the novel oxalic acid peroxide compositions of Structure A, include OO-(3-hydroxy-1,1-dimethylbutyl) O-methyl monoperoxyphthalate, OO-(3-hydroxy-1,1-dimethylbutyl) O-n-butyl monoperoxyphthalate, OO-(3-hydroxy-1,1-dimethylbutyl) O-ethyl monoperoxsuccinate and OO-(3-hydroxy-1,1-dimethylbutyl) O-n-butyl monoperoxglutarate.

Non-limiting examples of suitable hydroxyperoxides of Structure Y, where R=structure (c), useful for preparing the novel oxalic acid peroxide compositions of Structure A, include 2-methoxy-2-(3-hydroxy-1,1-dimethylpropylperoxy) propane, 2-methoxy-2-(3-hydroxy-1,1-dimethylbutylperoxy)propane and 1-methoxy-1-(3-hydroxy-1,1-dimethylbutylperoxy) cyclohexane.

Non-limiting examples of suitable hydroxyperoxides of Structure Y, where R=structure (d), useful for preparing the novel oxalic acid peroxide compositions of Structure A, include 3-hydroxy-1,1-dimethylbutyl 2-ethylperoxyhexanoate, 3-hydroxy-1,1-dimethylbutyl 2-ethylperoxybutyrate, 3-hydroxy-1,1-dimethylbutyl peroxypivalate, 3-hydroxy-1,1-dimethylbutyl peroxyneoheptanoate, 3-hydroxy-1,1-dimethylbutyl peroxyneodecanoate, 3-hydroxy-1,1-dimethylbutyl peroxyisobutyrate, 3-hydroxy-1,1-dimethylbutyl peroxypropionate, and 3-hydroxy-1,1-dimethylbutyl peroxyacetate.

Non-limiting examples of suitable oxalyl halides of Structure X, useful for preparing the novel oxalic acid peroxide compositions of Structure A, include oxalyl bromide, oxalyl chloride, methyl chlorooxalate, ethyl chlorooxalate, butyl chlorooxalate, dodecyl chlorooxalate, allyl chlorooxalate, phenyl chlorooxalate, cyclohexyl chlorooxalate and benzyl chlorooxalate. Novel oxalic acid peroxide compositions of Structure A', a reactive set of compounds of Structure A when n is 1 and Z is Cl or Br, are useful oxalyl halides in the synthetic processes of this invention. Compounds of Structure A' can react with water or alcohols (HO—$R^{13}$) in the presence of bases and optional solvents (followed by acidification when water is reacted) to form novel oxalate peroxides possessing the oxalate group [—O—C(O)C(O)—O—$R^{13}$]:

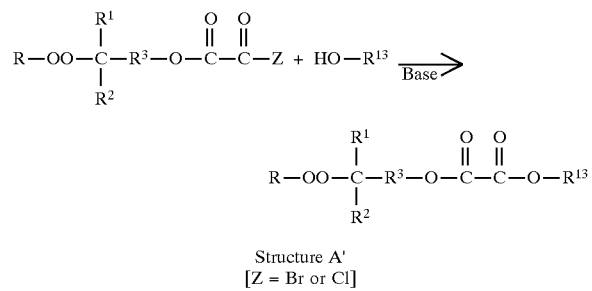

Structure A'
[Z = Br or Cl]

or A' can react with glycols (HO$R^{16}$OH) in the presence of optional bases and optional solvents to form novel oxalate peroxides possessing bis(oxalate) groups [—OC(O)C(O)—O$R^{16}$O—C(O)C(O)O—]:

2 A' + HOR$^{16}$OH ⟶

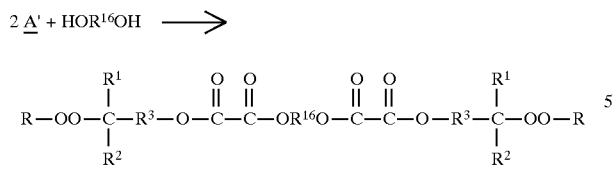

or A' can react with amines (HNR$^{13}$R$^{14}$) in the presence of optional bases and optional solvents to form novel peroxides possessing the oxamate group [—O—C(O)C(O)—NR$^{13}$R$^{14}$]:

A' + HNR$^{13}$R$^{14}$ $\xrightarrow{\text{Optional Base}}$

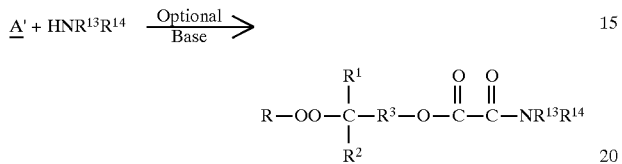

or A' can react with diamines (HNR$^{13}$R$^{16}$R$^{14}$NH) in the presence of optional bases and optional solvents to form novel peroxides possessing bis(oxamate) groups [—OC(O)C(O)—N(R$^{13}$)R$^{16}$N(R$^{14}$)—C(O)C(O)O—]:

2 A' + HN(R$^{13}$)R$^{16}$N(R$^{14}$)H ⟶

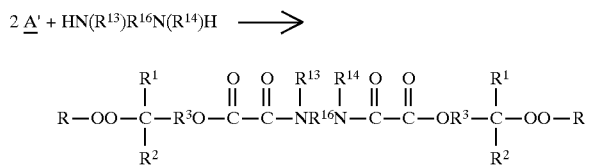

or A' can react with amino-alcohols (HNR$^{13}$R$^{16}$OH) in the presence of optional bases and optional solvents to form novel peroxides possessing oxamate-oxalate groups [—OC(O)C(O)—N(R$^{13}$)R$^{16}$—O—C(O)C(O)O—]:

2 A' + HN(R$^{13}$)R$^{16}$—OH ⟶

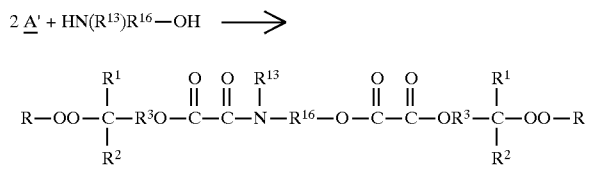

or A' can react with hydroperoxides (HOO—R) in the presence of bases and optional solvents to form novel peroxides possessing the monoperoxyoxalate group [—O—C(O)C(O)—OO—R]:

A' + HOO—R $\xrightarrow{\text{Base}}$ 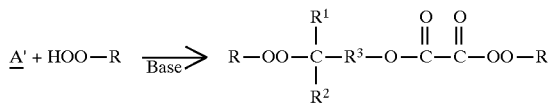

or A' can react with a hydroxy-peroxide of Structure N,

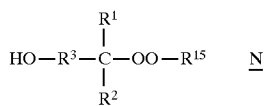 N in the presence of bases and optional solvents, to form novel unsymmetrical diperoxide oxalates:

A' + HO—R$^3$—C(R$^1$)(R$^2$)—OO—R$^{15}$ $\xrightarrow{\text{Base}}$

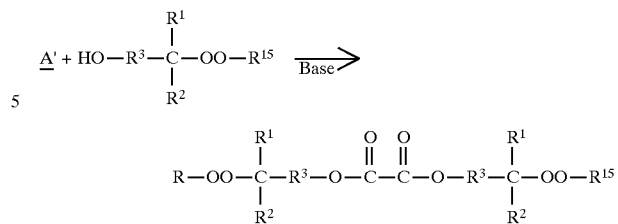

Non-limiting examples of suitable oxalyl halides of Structure A', useful for preparing the novel oxalate peroxides, oxamate peroxides, monoperoxyoxalate peroxides and unsymmetrical diperoxide oxalates of this invention, include 3-t-butylperoxy-1,1-dimethylbutyl chlorooxalate, 3-t-butylperoxy-1,1-dimethylpropyl chlorooxalate, 3-t-butylperoxy-1,1-dimethylbutyl bromooxalate, di-(3-chlorocarbonylcarbonyloxy-1,1-dimethylbutyl) peroxide, 3-chlorocarbonylcarbonyloxy-1,1-dimethylbutyl peroxy-2-ethylhexanoate, 3-chlorocarbonylcarbonyloxy-1,1-dimethylbutyl peroxyneoheptanoate, 3-chlorocarbonylcarbonyloxy-1,1-dimethylbutyl peroxy-2-methylbenzoate, OO-(3-chlorocarbonylcarbonyloxy-1,1-dimethylbutyl) O-ethyl monoperoxysuccinate and 2-(3-chlorocarbonylcarbonyloxy-1,1-dimethylbutylperoxy)-2-methoxypropane.

Non-limiting examples of suitable alcohols (HO—R$^{13}$), useful for reacting with A' to prepare the novel oxalate peroxides of Structure A, include methanol, isopropanol, butanol, dodecanol, cyclohexanol, allyl alcohol, methallyl alcohol, phenol, benzyl alcohol, 2-hydroxyethyl acrylate and methacrylate, ethylene glycol and butylene glycol.

Non-limiting examples of suitable diols (HO—R$^{16}$—OH), useful for reacting with A' to prepare the novel bis(oxalate) peroxides of Structure A, include ethylene glycol, 1,2-propanediol, 1,3-propanediol, 1,4-butanediol, 2,2-dimethyl-1,3-propanediol, resorcinol and catechol.

Non-limiting examples of suitable amines (HNR$^{13}$R$^{14}$), useful for reacting with A' to prepare the novel oxamate peroxides of Structure A, include methylamine, isopropylamine, butylamine, t-butylamine, dodecylamine, cyclohexylamine, allylamine, aniline and benzylamine.

Non-limiting examples of suitable diamines (HNR$^{13}$R$^{16}$R$^{14}$NH), useful for reacting with A' to prepare the novel bis(oxamate) peroxides of Structure A, include ethylene diamine and 1,6-diaminohexane.

Non-limiting examples of suitable amino-alcohols (HNR$^{13}$R$^{16}$OH), useful for reacting with A' to prepare the novel oxamate-oxalate peroxides of Structure A, include ethanolamine, N-methylethanolamine and propanolamine.

Non-limiting examples of suitable hydroperoxides (HOO—R), useful for reacting with A' to prepare the novel monoperoxyoxalate peroxides of Structure A, include t-butyl hydroperoxide, t-amyl hydroperoxide, t-hexyl hydroperoxide, 1,1,3,3-tetramethylbutyl hydroperoxide, 4-(t-butylperoxy)-1,1,4,4-tetramethylbutyl hydroperoxide, paramenthane hydroperoxide, and α-cumyl hydroperoxide.

Novel Oxalic Acid Peroxide Compositions of Structure A—Illustrative Examples

Non-limiting examples of the novel oxalic acid peroxide compositions of Structure A, in addition to those in the working examples, include the following:
3-t-Butylperoxy-1,1-dimethylpropyl chlorooxalate,
3-t-butylperoxy-1,1-dimethylbutyl bromooxalate,
3-chlorocarbonylcarbonyloxy-1,1-dimethylbutyl peroxy2-ethylhexanoate, 3-chlorocarbonylcarbonyloxy-1,1-dimethylbutyl peroxyneoheptanoate, 3-chlorocarbonylcarbonyloxy-1,1-dimethylbutyl peroxy-2-methylbenzoate,
OO-(3-chlorocarbonylcarbonyloxy-1,1-dimethylbutyl) O-ethyl monoperoxysuccinate,
2-(3-chlorocarbonylcarbonyloxy-1,1-dimethylbutylperoxy)-2-methoxypropane,
3-t-butylperoxy-1,1-dimethylpropyl hydrogen oxalate,
3-hydroxycarbonylcarbonyloxy-1,1-dimethylbutyl peroxy-2-ethylhexanoate,
3-hydroxycarbonylcarbonyloxy-1,1-dimethylbutyl peroxyneoheptanoate, 3-hydroxycarbonylcarbonyloxy-1,1-dimethylbutyl peroxy-2-methylbenzoate,
OO-(3-hydroxycarbonylcarbonyloxy-1,1-dimethylbutyl) O-ethyl monoperoxysuccinate,
di-(3-hydroxycarbonylcarbonyloxy-1,1-dimethylbutyl) peroxide,
3-t-butylperoxy-1,1-dimethylbutyl butyl oxalate,
OO-t-butyl O-(3-t-butylperoxy-1,1-dimethylbutyl) monoperoxyoxalate, OO-t-amyl O-(3-t-butylperoxy-1,1-dimethylbutyl) monoperoxyoxalate, OO-t-butyl O-(3-t-butylperoxy-1,1-dimethylpropyl) monoperoxyoxalate,
OO-α-cumyl O-(3-t-butylperoxy-1,1-dimethylbutyl) monoperoxyoxalate, OO-(4-t-butylperoxy-1,1,4,4-tetramethylbutyl) O-(3-t-butylperoxy-1,1-dimethylbutyl) monoperoxyoxalate,
3-t-butylperoxy-1,1-dimethylbutyl 3-(2-ethylhexanoylperoxy)-1,1-dimethylbutyl oxalate, and
3-t-butylperoxy-1,1-dimethylbutyl 3-(2-methylbenzoylperoxy)-1,1-dimethylbutyl oxalate, and the structures:

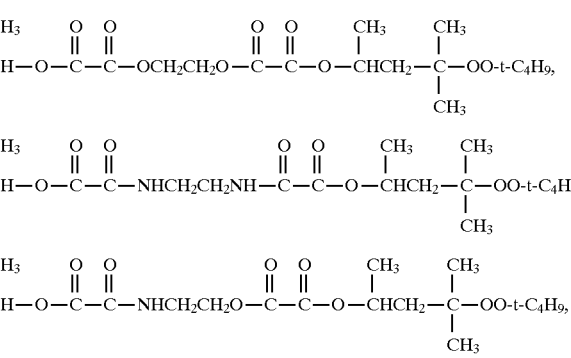

and

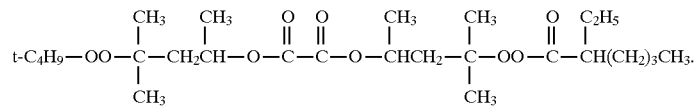

3-t-butylperoxy-1,1-dimethylpropyl butyl oxalate,
allyl 3-t-butylperoxy-1,1-dimethylpropyl oxalate,
3-t-butylperoxy-1,1-dimethylbutyl methyl oxalate,
3-t-butylperoxy-1,1-dimethylbutyl dodecyl oxalate,
3-t-butylperoxy-1,1-dimethylbutyl cyclohexyl oxalate,
3-t-butylperoxy-1,1-dimethylbutyl phenyl oxalate,
3-t-butylperoxy-1,1-dimethylbutyl 2-acryloyloxyethyl oxalate,
3-t-butylperoxy-1,1-dimethylbutyl benzyl oxalate,
di-(3-ethoxycarbonylcarbonyloxy-1,1-dimethylbutyl) peroxide,
di-(3-allyloxycarbonylcarbonyloxy-1,1-dimethylbutyl) peroxide,
OO-(3-butoxycarbonylcarbonyloxy-1,1-dimethylbutyl) O-ethyl monoperoxysuccinate,
N-butyl 3-t-butylperoxy-1,1-dimethylbutyl oxamate,
N-butyl 3-t-butylperoxy-1,1-dimethylpropyl oxamate,
N-allyl 3-t-butylperoxy-1,1-dimethylpropyl oxamate,
N-methyl 3-t-butylperoxy-1,1-dimethylbutyl oxamate,
N-dodecyl 3-t-butylperoxy-1,1-dimethylbutyl oxamate,
N-cyclohexyl 3-t-butylperoxy-1,1-dimethylbutyl oxamate,
N-phenyl 3-t-butylperoxy-1,1-dimethylbutyl phenyl oxamate,
3-t-butylperoxy-1,1-dimethylbutyl oxamate,
di-(3-allylaminocarbonylcarbonyloxy-1,1-dimethylbutyl) peroxide,
OO-(3-butylaminocarbonylcarbonyloxy-1,1-dimethylbutyl) O-ethyl monoperoxysuccinate, Novel Oxalic Acid Peroxide Compositions of Structure A—Utility A. Polymerization of Ethylenically Unsaturated Monomers In the free-radical polymerizations of ethylenically unsaturated monomers at suitable temperatures and pressures the novel oxalic acid peroxide compositions of Structure A of this invention were found to be effective initiators with respect to efficiency (reduced initiator requirements, etc.). Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether;

allyl esters, such as allyl acetate, allyl benzoate, allyl ethyl carbonate, triallyl phosphate, diallyl phthalate, diallyl fumarate, diallyl glutarate, diallyl adipate, diallyl carbonate diethylene glycol bis(allyl carbonate) (i.e., ADC); acrolein; methyl vinyl ketone; or mixtures thereof.

Temperatures of 0° C. to 180° C., preferably 20° C. to 160° C., more preferably 30° C. to 150° C. and levels of novel oxalic acid peroxide compositions of Structure A (on a pure basis) of 0.002 to 3%, preferably 0.005% to 1%, more preferably 0.01% to 0.75% by weight based on monomer, are normally employed in conventional polymerizations and copolymerizations of ethylenically unsaturated monomers. The novel oxalic acid peroxide compositions of this invention can be used in combination with other free-radical initiators such as those disclosed at the bottom of column 4 and the top of column 5 of U.S. Pat. No. 4,525,308. Using the peroxide compositions of this invention in combination with these initiators adds flexibility to the processes of polymer producers and allows them to "fine tune" their polymerization processes.

B. Curing of Unsaturated Polyester Resins

In the curing of unsaturated resin compositions by heating at suitable curing temperatures in the presence of free-radical curing agents, the novel oxalic acid peroxide compositions of Structure A of this invention exhibit enhanced curing activity in the curable unsaturated polyester resin compositions. Unsaturated polyester resins that can be cured by the novel oxalic acid peroxide compositions of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,4,4-trimethyl-1,3-pentanediol, glycerol, pentaerythritol, mannitol and others. Mixtures of such di- or polyacids and/or mixtures of such di- or polyols may also be used. The di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2, 3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are copolymerizable with said unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene.

Other types of unsaturated polyester resin compositions can be cured using the novel oxalic acid peroxide compositions of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with appropriate amounts of a bisphenol such as Bisphenol A [2,2-(4-hydroxyphenyl)propane], in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. and levels of novel oxalic acid peroxide compositions of Structure A of about 0.05% to 5% or more, preferably 0.10% to 4%, more preferably 0.25% to 3% by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

C. Curing of Elastomers and Crosslinking of Thermoplastic Polymers

In the curing of elastomeric compositions, and the crosslinking of polymer compositions, by heating at suitable curing and crosslinking temperatures in the presence of free-radical curing and crosslinking agents, the novel oxalic acid peroxide compositions of this invention exhibit curing and crosslinking activities.

Elastomeric resin compositions that can be cured by the novel oxalic acid peroxide compositions of this invention include elastomers such as ethylene-propylene copolymers (EPR), ethylene-propylene-diene terpolymers (EPDM), polybutadiene (PBD), silicone rubber (SR), nitrile rubber (NR), neoprene, fluoroelastomers and ethylene-vinyl acetate copolymer (EVA).

Polymer compositions that can be crosslinked by the novel oxalic acid peroxide compositions of this invention include olefin thermoplastics such as chlorinated polyethylene (CPE), low density polyethylene (LDPE), linear-low density polyethylene (LLDPE), and high density polyethylene (HDPE).

Temperatures of about 80° C. to 310° C. and novel oxalic acid peroxide composition levels of about 0.1% to 10%, preferably 0.5% to 5%, based on weight of curable elastomeric resin composition or crosslinkable olefin polymer composition, are normally employed.

The curable elastomeric resin composition or crosslinkable polymer composition can be optionally filled with the materials listed above for use with the conventional unsaturated polyester resin compositions.

D. Modification of Propylene Homo- and Copolymers

In the processes for modifying propylene homopolymers and propylene copolymers (e.g., beneficial degradation of polypropylene (PP) by reducing the polymer molecular weight and the polymer molecular weight distribution), the novel oxalic acid peroxide compositions of this invention exhibit polypropylene modification activity.

Temperatures of about 140° C. to 340° C. and novel oxalic acid peroxide composition levels of about 0.01% to 1.0% based on weight of modifiable propylene homopolymers and propylene copolymers are normally employed. Optionally, up to 1% by weight of molecular oxygen can be employed as a modification co-catalyst.

Novel Oxalic Acid Peroxide Compositions of Structure A—Preparative and Utility Examples The following examples further illustrate the best mode contemplated by the inventors for practicing the instant invention, and are presented to provide detailed preparative and utility illustrations of the invention and are not intended to limit the breadth and scope of the invention.

EXAMPLE 1

Preparation of 3-t-Butylperoxy-1,3-dimethylbutyl Ethyl Oxalate (I-1)

A 125 mL Erlenmeyer flask equipped with a magnetic stirring bar was charged with 10.0 g (48.4 mmoles) of 92% 3-t-butylperoxy-1,3-dimethylbutanol, 7.8 g (77.2 mmoles) of triethylamine, 0.1 g (0.08 mmole) of 4-dimethylaminopyridine and 30 g of dry ethyl acetate. A clear solution resulted at room temperature. To this vigorously stirred solution at room temperature was slowly added a solution consisting of 7.0 g (50.2 mmoles) of ethyl oxalyl chloride and 10 g of dry ethyl acetate over a period of 20 minutes. A precipitate immediately formed and the flask became warm. It was necessary to cool the flask in order to maintain the temperature around room temperature. After a total reaction period of 60 minutes, the reaction mass was transferred to a separatory funnel, 100 mL of water was added to the reaction mass and shaken. The aqueous phase was separated and discarded. The organic phase was washed once with aqueous 10% HCl solution, twice with water and once with dilute aqueous $NaHCO_3$ solution. The resulting solution was dried over about 10% by weight of anhydrous $MgSO_4$, and, after separation of the spent desiccant by filtration, the solvent was removed in vacuo leaving 13.9 g (99% of theory, uncorrected) of a clear yellow liquid. The product contained 5.79% active oxygen (theory, 5.51%), therefore, compound I-1, was obtained with an assay of 100% and in a corrected yield of 99%. Gas chromatographic analysis showed that the product contained less than 0.1% of 3-t-butylperoxy-1,3-dimethylbutanol, the starting material. An infrared (IR) spectrum of the product showed carbonyl bands at 1770 $cm^{-1}$ and 1745 $cm^{-1}$ and a peroxide (—OO—) band at 870 $cm^{-1}$.

EXAMPLE 2

Preparation of 3-t-Butylperoxy-1,3-dimethylbutyl Chlorooxalate (I-2)

A 250 mL three-neck flask equipped with a magnetic stirrer, a thermometer and an addition funnel was charged with 25.4 g (200 mmoles) of oxalyl chloride and 75 mL of methyl t-butyl ether (MTBE). Then to the resulting solution was added 20.6 g (100 mmoles) of 93% 3-t-butylperoxy-1, 3-dimethylbutanol over a period of 30 minutes at 22°–28° C. The addition funnel was then replaced with a nitrogen gas tube and dry nitrogen gas was slowly bubbled through the reaction mass in order to remove HCl over a period of 4 hours at 25°–30° C. The MTBE, excess oxalyl chloride, and any remaining gas were removed in vacuo using a water aspirator. Obtained was 28.3 g (101% of theory, uncorrected) of a yellow liquid. An IR spectrum of the product showed no OH bands and showed carbonyl bands at 1800 $cm^{-1}$ and 1760 $cm^{-1}$. The assay of I-2, based upon hydrolyzable chloride content (theory, 12.63%; found, 12.37%), was 97.9% and the corrected yield was 98.6%.

EXAMPLE 3

Preparation of 3-t-Butylperoxy-1,3-dimethylbutyl Hydrogen Oxalate (I-3)

A 50 mL Erlenmeyer flask equipped with a magnetic stirrer and a thermometer was charged with 50 g of water and 2.8 g (10 mmoles) of 3-t-butylperoxy-1,3-dimethylbutyl chlorooxalate and the resulting mixture was stirred at room temperature. No reaction appeared to be occurring, therefore, 2.1 g (23 mmoles) of $NaHCO_3$ was added. Gas evolution occurred and the organic liquid dissolved in the aqueous phase at room temperature. The pH of the solution was about 9. The aqueous solution was washed twice with 30 mL portions of MTBE in order to remove neutral impurities. Then the aqueous solution was acidified with 20 g (27 mmoles) of aqueous 5% HCl solution and a yellow organic liquid formed. The resulting mixture was extracted twice with 30 mL portions of MTBE. The MTBE extracts were combined, washed once with 50 mL of water, dried over 5% by weight of anhydrous $MgSO_4$, and, after separation of the spent desiccant by filtration, the solvent was removed in vacuo leaving 2.2 g (85% of theory, uncorrected) of a clear yellow liquid. An IR spectrum of the product showed an acid OH band at about 3200 $cm^{-1}$, a very strong carbonyl band at 1740 $cm^{-1}$ and a peroxide (—OO—) band at about 875 $cm^{-1}$.

Based on the method of preparation, yield data, and IR data the product obtained in this reaction was I-3.

EXAMPLE 4

Preparation of Allyl 3-t-Butylperoxy-1,3-dimethylbutyl Oxalate (I-4)

A 100 mL 3-necked flask equipped with a magnetic stirring bar, a nitrogen inlet line, a thermometer and an addition funnel was charged with 12.6 g (97.3 mmoles) of oxalyl chloride and the flask contents were cooled to 0° C. Then 10.0 g (48.7 mmoles) of 92.6% 3-t-butylperoxy-1,3-dimethylbutanol was added dropwise over 30 minutes while the flask was swept with a steady stream of dry nitrogen. After the addition was completed the reaction mass was stirred for 60 minutes at room temperature. A vacuum line was then attached to the flask in order to distill off the excess oxalyl chloride, however, this was only partially successful. The contents in the flask were diluted with dry ethyl acetate and the contents were then transferred to a one-necked flask. The solvent and excess oxalyl chloride were then removed using a rotary evaporator. Obtained was a light yellow oil which was cooled to 10° C. and to it was added 3.0 g (51.7 mmoles) of allyl alcohol over a period of 10 minutes while a vigorous stream of dry nitrogen was swept through the reaction mass. The reaction mixture was then diluted with ethyl acetate and the solution was stripped on a rotary evaporator to remove solvent, HCl and residual allyl alcohol. Obtained was 11.9 g (81% of theory, uncorrected of a light yellow liquid. Gas chromatography (GC) showed a single large peak having an area % of 98.6. An IR spectrum of the product showed carbonyl bands at 1770 cm$^{-1}$ and 1750 cm$^{-1}$ and a peroxide (—OO—) band at 875 cm$^{-1}$.

Based on the method of preparation, yield data, GC data, and IR data the product obtained in this reaction was I-4.

A second preparation of I-4 was carried out. A 100 mL 3-necked flask equipped with a magnetic stirring bar, a nitrogen inlet line, a thermometer and an addition funnel with a side arm was charged with 25.9 g (200 mmoles) of oxalyl chloride, dry nitrogen gas was bubbled through the oxalyl chloride and the flask contents were cooled to 0° C. Then 20.0 g (97.3 mmoles) of 92.6% 3-t-butylperoxy-1,3-dimethylbutanol was added dropwise at such a rate that the temperature remained below 15° C. The addition took 30 minutes to complete. The reaction mass was then stirred for 60 minutes at 15° C. after which 50 mL of dry ethyl acetate was added. The contents were then transferred to a one-necked flask and the solvent and excess oxalyl chloride were then removed using a rotary evaporator. Obtained was 29.3 g of a light yellow oil. The oil was cooled to 10° C. and to it was added 6.0 g (103.3 mmoles) of allyl alcohol over a period of 15 minutes while a vigorous stream of dry nitrogen was swept through the reaction mass. The temperature was held below 20° C. during the addition of allyl alcohol. The reaction mixture was then stirred for 60 minutes at 15°–20° C. after which it was stripped on a rotary evaporator. Obtained was 31.7 g (>100% of theory, uncorrected) of a light yellow liquid. GC showed a single large peak, 93% by area. An IR spectrum of the product showed carbonyl bands at 1770 cm$^{-1}$ and 1750 cm$^{-1}$ and a peroxide (—OO—) band at 875 cm$^{-1}$.

In order to prepare a high purity sample of I-4, 11.9 g of the first preparation and 23 g of the second preparation were combined and purified by preparative liquid chromatography using a Walters Prep 500 Liquid Chromatograph. Obtained was 30.3 g of I-4 having a purity of 97.6% according to GC analysis.

EXAMPLE 5

Preparation of a mixture of Diallyl Oxalate Di-(3-t-Butylperoxy-1,3-dimethylbutyl) Oxalate and Allyl 3-t-Butylperoxy-1,3-dimethylbutyl Oxalate (I-4)

A 250 mL 3-necked flask equipped with a magnetic stirring bar, a nitrogen inlet line, a thermometer and an addition funnel was charged with 4.3 g (30.2 mmoles) of oxalyl chloride and 75 mL of MTBE and the flask contents were cooled to 0° C. Then a solution of 6.8 g (33.1 mmoles) of 92.6% 3-t-butylperoxy-1,3-dimethylbutanol and 3.4 g (33.6 mmoles) of triethylamine in 10 mL of MTBE was added dropwise over 60 minutes at 0°–5° C. and the solution was stirred for an additional 30 minutes after the addition was completed. Then a solution of 1.9 g (32.4 mmoles) of allyl alcohol and 3.4 g (33.6 mmoles) of triethylamine in 10 mL of MTBE was added to the flask contents over a period of 30 minutes. The reaction mixture was then stirred at room temperature for 120 minutes after which the reaction was quenched with water. The aqueous phase was separated and discarded. The organic phase was washed once with aqueous 10% HCl solution, three times with water and once with dilute aqueous NaHCO$_3$ solution. The product solution was dried over 5% by weight of anhydrous MgSO$_4$, and, after separation of the spent desiccant by filtration, the solvent was removed in vacuo leaving 9.4 g (96% of theory, uncorrected) of a clear yellow liquid. An IR spectrum of the product showed carbonyl bands at 1770 cm$^{-1}$ and 1750 cm$^{-1}$ and a peroxide (—OO—) band at 875 cm$^{-1}$. GC showed three product peaks at retention times of 21.6 minutes (6% by area, assigned to diallyl oxalate), 33.4 minutes (65% by area, assigned to allyl 3-t-butylperoxy-1,3-dimethylbutyl oxalate) and 43.6 minutes [15% by area, assigned to di-(3-t-butylperoxy-1,3-dimethylbutyl) oxalate]. GC also showed that the product mixture contained less than 0.1% allyl alcohol and only 0.2% 3-t-butylperoxy-1,3-dimethylbutanol.

Based on the method of preparation, yield data, GC data, and IR data the product obtained in this reaction was the desired title product mixture.

EXAMPLE 6

Preparation of 3-t-Butylperoxy-1,3-dimethylbutyl 3-Neoheptanoylperoxy-1,3-dimethylbutyl Oxalate (I-5)

A 250 mL 3-necked flask equipped with a magnetic stirring bar, a nitrogen inlet line, a thermometer and an addition funnel was charged with 75 mL of MTBE and 2.5 g (19.3 mmoles) of oxalyl chloride and the flask contents were cooled to 0° C. Then a solution of 3.9 g (19 mmoles) of 92.6% 3-t-butylperoxy-1,3-dimethylbutanol and 1.5 g (19.0 mmoles) of pyridine in 10 mL of MTBE was added dropwise over 30 minutes while the temperature was maintained at 0°–5° C. After the addition was completed the reaction mass was stirred for 60 minutes at 0°–5° C. To the stirred reaction mass was added a solution of 5.0 g (19.2 mmoles) of 94.4% 3-hydroxy- 1,1-dimethylbutyl peroxyneoheptanoate and 1.5 g (19.0 mmoles) of pyridine in 10 mL of MTBE over a period of 15 minutes. The reaction mixture was then stirred for an additional 45 minutes at 20°–25° C. after which it was quenched with water. After separating and discarding the aqueous phase the organic was washed once with cold aqueous 10% HCl solution, three times with water and once with dilute aqueous NaHCO$_3$ solution. The product solution was dried over 5% by weight of anhydrous MgSO$_4$, and, after separation of the spent desiccant by filtration, the solvent was removed in vacuo leaving 9.3 g (100% of theory, uncorrected) of a hazy colorless oil. The product contained 6.78% active oxygen (theory, 6.52%), therefore, I-5 was obtained with an assay of 100% and in a corrected yield of 100%. A Differential Scanning Calorimeter (DSC) scan showed two peroxide decomposition temperatures, one at 71° C. for the 3-neoheptanoylperoxy-1,3-dimethylbutyl moiety and one at 169° C. for the 3-t-butylperoxy-1,3-dimethylbutyl moiety.

EXAMPLE 7

Preparation of OO-(1,1,3,3-Tetramethylbutyl) O-(3-t-Butylperoxy-1,3-dimethylbutyl) Monoperoxyoxalate (I-6)

A 250 mL 3-necked flask equipped with a magnetic stirring bar, a condenser, a thermometer and an addition funnel and cooled with an ice bath was charged with 3.1 g (20.0 mmoles) of 94% 1,1,3,3-tetramethylbutyl hydroperoxide, 2.4 g (30.0 mmoles) of dry pyridine and 50 mL of MTBE. The flask contents were cooled to 3° C. Then to the resulting vigorously stirred solution at 3°–7° C. was added a solution of 5.6 g (20.0 mmoles) of 3-t-butylperoxy-1,3-dimethylbutyl chlorooxalate over a period of 11 minutes. A solid, pyridinium chloride, formed shortly after the addition commenced. After the addition was completed the reaction mass was stirred for 90 minutes at 2° C. after which 10 mL of water was added and the reaction mass was stirred an additional 15 minutes. The aqueous layer was then separated and the organic layer was washed once with 50 mL of water, three times with 40 mL portions of aqueous 5% HCl solution and once with 50 mL of saturated aqueous NaHCO$_3$ solution. The product solution was dried over 10% by weight of anhydrous MgSO$_4$, and, after separation of the spent desiccant by filtration, the solvent was removed in vacuo leaving 6.3 g (81% of theory, uncorrected) of a colorless liquid. An IR spectrum of the product showed an OH band at about 3480 cm$^{-1}$, a monoperoxyoxalate carbonyl band at 1800 cm$^{-1}$, an oxalate carbonyl band at 1750 cm$^{-1}$ and a peroxide (—OO—) band at about 875 cm$^{-1}$. The presence of the OH band at 3480 cm$^{-1}$ in the IR spectrum of the product indicated the presence of a hydroxy-containing impurity. Therefore, the product was taken up in 60 mL of MTBE and the resulting solution was washed with 50 mL of water containing 4.0 g of NaHSO$_3$ and once with 50 mL of saturated aqueous NaH$_2$PO$_4$ solution. After drying and isolation of the product as above, 5.5 g (71% of theory, uncorrected) of colorless oil was obtained. The IR spectrum of the purified product showed no OH band in the 3500 cm$^{-1}$ region, a monoperoxyoxalate carbonyl band at 1800 cm$^{-1}$, an oxalate carbonyl band at 1750 cm$^{-1}$ and a peroxide (—OO—) band at about 880 cm$^{-1}$. The IR spectrum of the purified product was that expected for the desired titled product. Liquid chromatographic (LC) analysis of the product showed a single large peak. The product contained 2.33% active oxygen according to a peroxyester active oxygen method (theory, 4.10%).

Based on the method of preparation, yield data, LC data, and IR data the product obtained in this reaction was I-6. The product was a sequential diperoxide having a dialkyl peroxide moiety with a 10 Hr half-life temperature of about 120° C. and a monoperoxyoxalate moiety having a 10 Hr half-life temperature of about 35°–40° C.

EXAMPLE 8

Preparation of Di(3-chlorocarbonylcarbonyloxy-1,1-dimethylbutyl) Peroxide (I-7)

A 250 mL three-neck flask equipped with a magnetic stirrer, a thermometer and an addition funnel was charged with 50.8 g (400 mmoles) of oxalyl chloride and 75 mL of MTBE. Then to the resulting solution was slowly added 24.7 g (100 mmoles) of 95% di(3-hydroxy-1,1-dimethylbutyl) peroxide over a period of 30 minutes at 21°–30° C. The addition funnel was then replaced with a nitrogen gas tube and dry nitrogen gas was slowly bubbled through the reaction mass in order to remove HCl over a period of 4 hours at 25°–30° C. The MTBE, excess oxalyl chloride, and any remaining gas were removed in vacuo using a water aspirator. Obtained was 38.2 g (97% of theory, uncorrected) of a amber liquid. An IR spectrum of the product showed no OH bands and showed a pair of carbonyl bands at 1790 cm$^{-1}$ and 1755 cm$^{-1}$. Based on hydrolyzable chloride content the assay of the product was 85.0% and the corrected yield was 82.7%.

Based on the method of preparation, assay data, yield data, and IR data the product obtained in this reaction was I-7.

EXAMPLE 9

Preparation of N-t-Butyl 3-t-Butylperoxy-1,3dimethylbutyl Oxamate (I-8)

A 250 mL 3-necked flask equipped with a magnetic stirring bar, a nitrogen inlet line, a thermometer and an addition funnel was charged with 40 mL of MTBE, 2.5 g (34 mmoles) of t-butylamine and 4.0 g (50 mmoles) of pyridine. The flask contents were cooled to 10° C. Then 5.7 g (20 mmoles) of 98.1% 3-t-butylperoxy-1,3-dimethylbutyl chlorooxalate (I-2) in 10 mL of MTBE was added dropwise over 15 minutes at 10°–20° C. to the stirred solution. After the addition was completed the reaction mass was stirred for 60 minutes at 15°–20° C. Then 50 mL of water and 20 mL of MTBE were added to the stirred reaction mass and the mixture was allowed to separate into liquid phases. The aqueous layer was separated and discarded. The organic layer was washed twice with 50 g portions of aqueous 5% hydrochloric acid solution and then with 50 mL portions of water until the pH was about 7. The product solution was dried over 5% by weight of anhydrous MgSO$_4$, and, after separation of the spent desiccant by filtration, the solvent was removed in vacuo leaving 3.1 g (49% of theory, uncorrected) of a liquid product. An IR spectrum of the product showed a weak-medium pair of bands in the 3400–3500 cm$^{-1}$ region due to the NH group, a strong carbonyl band at 1705 cm$^{-1}$ and weaker carbonyl shoulder bands at about 1730 cm$^{-1}$ and about 1760 cm$^{-1}$.

Based on the method of preparation and IR data the product obtained in this reaction was I-8.

EXAMPLE 10

Crosslinking Efficiency of 3-t-Butylperoxy-1,3-dimethylbutyl Ethyl Oxalate (I-1) in High Density Polyethylene (HDPE)

Compound I-1 was evaluated for crosslinking efficiency in HDPE compared to 2,5-dimethyl-2,5-di(t-butylperoxy)-3-hexyne (LUPERSOL 130, manufactured by ELF ATOCHEM North America, Inc.). I-1 and LUPERSOL 130 were individually blended into samples of HDPE (USI's LY 66000 HDPE) at 140° C. using a Brabender for thorough mixing. The level of crosslinking agent employed was 10 meq (milliequivalents of peroxide) per hundred grams of HDPE resin. This amounted to 2.904 grams of I-1 per hundred grams of HDPE resin and 1.43 grams of LUPERSOL 130 per hundred grams of HDPE resin. Disks of the compounded HDPE resins were pressed out and these resin disks were used for determining crosslinking data using a Monsanto Oscillating Disk Rheometer (ODR) at 196.1° C. (385° F.), ±3° arc. The crosslinking data obtained are summarized in the table below:

| CROSSLINKING OF HDPE AT 385° F. | | |
| --- | --- | --- |
| FORMULATION: | A | B |
| LUPERSOL 130 (10 meq/100 g HDPE) | 1.43 | — |
| I-1 (10 meq/100 g HDPE) | — | 2.904 |
| M$_H$ (in-lbs) | 34.6 | 40.3 |
| M$_H$–M$_L$ (in-lbs) | 33.4 | 38.6 |
| T$_{C90}$ (mins) | 8.4 | 5.6 |
| T$_{S2}$ (mins) | 1.8 | 1.4 |

Based on cure times (T$_{C90}$) and torque enhancement (M$_H$–M$_L$) the results show that 3-t-butylperoxy-1,3-dimethylbutyl ethyl oxalate (I-1) was a faster and a much more efficient crosslinking agent for HDPE than was LUPERSOL 130, the crosslinking agent currently employed to commercially crosslink HDPE. Consequently, the results showed that I-1 was a very good crosslinking peroxide candidate for HDPE.

EXAMPLE 11

Crosslinking Efficiency of 3-t-Butylperoxy-1,3-dimethylbutyl Ethyl Oxalate (I-1) in Low Density Polyethylene (LDPE)

Compound I-1 was evaluated for crosslinking efficiency in LDPE compared to 2,5-dimethyl-2,5-di(t-butylperoxy)hexane (LUPERSOL 101, manufactured by ELF ATOCHEM North America, Inc.). I-1 and LUPERSOL 101 were individually blended into samples of LDPE (Union Carbide DYNH-1) at 120° C. using a Brabender for thorough mixing. The level of crosslinking agent employed was 10 meq (milliequivalents of peroxide) per hundred grams of LDPE resin. This amounted to 2.904 grams of I-1 per hundred grams of LDPE resin and 1.45 grams of LUPERSOL 101 per hundred grams of LDPE resin. Disks of the compounded LDPE resins were pressed out and these resin disks were used for determining crosslinking data using a Monsanto Oscillating Disk Rheometer (ODR) at 196.1° C. (385° F.), ±3°arc. The crosslinking data obtained are summarized in the table below:

| CROSSLINKING OF LDPE AT 385° F. | | |
|---|---|---|
| FORMULATION: | A | B |
| LUPERSOL 101 (10 meq/100 g LDPE) | 1.45 | — |
| I-1 (10 meq/100 g LDPE) | — | 2.904 |
| $M_H$ (in-lbs) | 24.0 | 28.3 |
| $M_H$–$M_L$ (in-lbs) | 21.5 | 25.8 |
| $T_{C90}$ (mins) | 8.9 | 10.4 |
| $T_{S2}$ (mins) | 2.15 | 2.30 |

Based on torque enhancement ($M_H$–$M_L$) the results show that I-1 was a much more efficient crosslinking agent for LDPE than was LUPERSOL 101, a crosslinking agent currently employed to commercially crosslink LDPE. In addition, use of I-1 as a crosslinking agent for LDPE advantageously resulted in a longer scorch time ($T_{S2}$) than when LUPERSOL 101 was employed. Consequently, the results showed that I-1 was a very good crosslinking peroxide candidate for LDPE.

EXAMPLE 12

Polypropylene (PP) Modification Efficiency of 3-t-Butylperoxy-1,3-dimethylbutyl Ethyl Oxalate (I-1)

Compound I-1 was evaluated for polypropylene (PP) modification efficiency compared that of to 2,5-dimethyl-2,5-di(t-butyl-peroxy)hexane (LUPERSOL 101, manufactured by ELF ATOCHEM North America, Inc.). I-1 and LUPERSOL 101 were separately blended under a blanket of nitrogen gas (to eliminate the effect of oxygen on modification of PP) into PP (Himont 6501), containing:

0.1% calcium stearate 0.3% dilaury thiodipropionate 0.1% Irganox 1010 (manufactured by Ciba Geigy Corp.) at 180° C. using a Brabender plastigraph. Mixing under the blanket of nitrogen gas was continued for a total of 10 minutes. In these experiments, the level of modifying agent employed was 0.20 meq (milliequivalent of peroxide) per hundred grams of PP resin. This amounted to 0.058 grams of I-1 per hundred grams of PP resin and 0.029 grams of LUPERSOL 101 per hundred grams of PP resin. Melt flow index (MFI) is a measure of the amount of degradation (modification or molecular weight reduction) of PP. The higher the MFI of the modified PP resin under specific conditions, the lower the molecular weight of the PP resin. The MFI data for the virgin PP resin and the modified PP resins were determined according to ASTM D-1238 (230° C., 2.16 kg weight). The MFI data are summarized below:

| PP Modifying Agent | Peroxide Weight, % | Peroxide meq per 100 g PP | MFI grams/10 mins. |
|---|---|---|---|
| None | — | — | 5.5 |
| LUPERSOL 101 | 0.029 | 0.20 | 11.5 |
| I-1 | 0.058 | 0.20 | 15.5 |

The results showed that 3-t-butylperoxy-1,3-dimethylbutyl ethyl oxalate (I-1) was much more efficient for modifying PP than was LUPERSOL 101. Lupersol 101 is currently the most widely used commercial modifying agent for PP. Consequently, the results showed that I-1 was a very good modifying agent for PP.

EXAMPLE 13

Crosslinking Efficiency of Allyl 3-t-Butylperoxy-1,3-dimethylbutyl Oxalate (I-4) in High Density Polyethylene (HDPE)

Compound I-4 was evaluated for crosslinking efficiency in HDPE compared to 2,5-dimethyl-2,5-di(t-butylperoxy)-3-hexyne (LUPERSOL 130, manufactured by ELF ATOCHEM North America, Inc.). I-4 and LUPERSOL 130 were individually blended into samples of HDPE (USI LY 66000) at 140° C. using a Brabender mixer. The level of crosslinking agent employed was 10 meq (milliequivalents of peroxide) per hundred grams of HDPE resin. This amounted to 3.024 grams of I-4 per hundred grams of HDPE resin and 1.432 grams of LUPERSOL 130 per hundred grams of HDPE resin. Disks of the compounded HDPE resins were pressed out and these resin disks were used for determining crosslinking data using a Monsanto Oscillating Disk Rheometer (ODR) at 385° F., ±3° arc. The crosslinking data obtained are summarized in the table below:

| CROSSLINKING OF HDPE AT 385° F. | | |
|---|---|---|
| FORMULATION: | A | B |
| LUPERSOL 130 (10 meq/100 g HDPE) | 1.432 | — |
| I-4 (10 meq/100 g HDPE) | — | 3.024 |
| $M_H$ (in-lbs) | 36.8 | 45.5 |
| $M_H$–$M_L$ (in-lbs) | 35.3 | 43.9 |
| $T_{C90}$ (mins) | 9.8 | 5.5 |
| $T_{S2}$ (mins) | 1.9 | 1.5 |

Based on cure times ($T_{C90}$) and torque enhancement ($M_H$–$M_L$) the results show that I-4 was a faster and a much more efficient crosslinking agent for HDPE than was LUPERSOL 130, the crosslinking agent currently employed to commercially crosslink HDPE. Consequently, the results showed that I-4 was a very good crosslinking peroxide candidate for HDPE.

The subject matter regarded by the applicants as their invention is particularly pointed out and distinctly claimed as follows:

We claim:

1. A peroxide composition of Structure A:

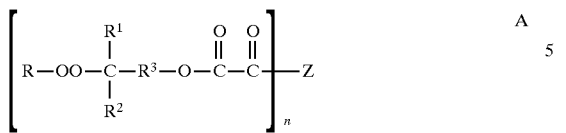

where n is 1 or 2, and R is selected from the group consisting of a t-alkyl radical of 4 to 12 carbons, a t-cycloalkyl radical of 6 to 13 carbons, a t-alkynyl radical of 5 to 9 carbons, a t-aralkyl radical of 9 to 13 carbons and the structures (a), (b), (c), (d) and (e),

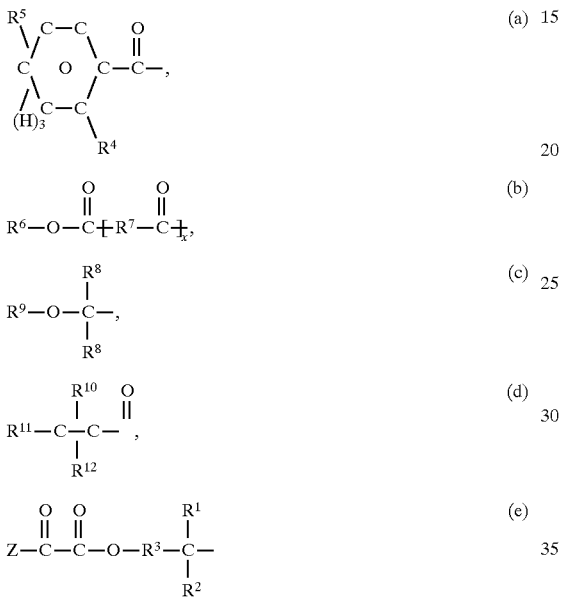

where $R^4$ and $R^5$ are the same or different and are selected from the group consisting of hydrogen, lower alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, hydroxy, fluoro, chloro or bromo, and, x is 0 or 1, $R^6$ is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6–10 carbons, hydroxy, chloro, bromo or cyano, and a substituted or unsubstituted cycloalkyl radical of 5 to 12 carbons optionally having an oxygen atom or a nitrogen atom in the cycloalkane ring, with substituents being one or more lower alkyl radicals of 1 to 4 carbons, and, $R^7$ is selected from a substituted or unsubstituted alkylene diradical of 2 to 3 carbons, substituents being one or more lower alkyl radicals of 1 to 4 carbons, and substituted or unsubstituted 1,2-, 1,3- and 1,4-phenylene diradicals, substituents being one or more lower alkyl radicals of 1 to 4 carbons, chloro, bromo, nitro or carboxy, and, $R^8$ is a lower alkyl radical of 1 to 4 carbons, and, additionally, the two $R^8$ radicals may be concatenated to form an alkylene diradical of 4 to 5 carbons, and, $R^9$ is a lower alkyl radical of 1 to 4 carbons, and, $R^{10}$, $R^{11}$, and $R^{12}$ can be the same or different and are selected from the group consisting of hydrogen, alkyl radicals of 1 to 8 carbons, aryl radicals of 6 to 10 carbons, alkoxy radicals of 1 to 8 carbons and aryloxy radicals of 6 to 10 carbons, and, $R^1$ and $R^2$ are lower alkyl radicals of 1 to 4 carbons, and, when R is selected from a t-alkyl radical of 4 to 12 carbons $R^2$ can additionally be a t-alkylperoxy radical of 4 to 12 carbons, $R^3$ is selected from the group consisting of a substituted or unsubstituted alkylene diradical of 2 to 4 carbons and a substituted or unsubstituted alkynylene diradical of 2 to 4 carbons, substituents being one or more lower alkyl radicals of 1 to 4 carbons, and, when n is 1, Z is selected from the group consisting of $OR^{13}$, $NR^{13}R^{14}$, OO—R, Cl and Br, where $R^{13}$ and $R^{14}$ are the same or different and are selected from the group consisting of hydrogen, substituted or unsubstituted alkyl radicals of 1 to 18 carbons, substituents being one or more alkyl radicals of 1 to 6 carbons, alkoxy radicals of 1 to 6 carbons, aryloxy radicals of 6 to 10 carbons, acryoyloxy radicals, methacryloyloxy radicals, chloro, bromo and cyano, substituted or unsubstituted alkenyl radicals of 3 to 12 carbons, substituents being one or more lower alkyl radicals of 1 to 4 carbons, substituted or unsubstituted aryl radicals of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, substituted or unsubstituted aralkyl radicals of 7 to 11 carbons, substituents being one or more alkyl radicals of 1 to 6 carbons, alkoxy radicals of 1 to 6 carbons, aryloxy radicals of 6 to 10 carbons, chloro, bromo and cyano, and substituted or unsubstituted cycloalkyl radicals of 5 to 12 carbons optionally having an oxygen atom or a nitrogen atom in the cycloalkane ring, with substituents being one or more lower alkyl radicals of 1 to 4 carbons, and Z is also selected from structure (g),

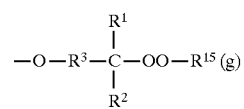

$R^{15}$ is selected from the definitions of R, with the proviso that R and $R^{15}$ are not the same, and when n is 2, Z is selected from the group consisting of structures (h), (i), and (j),

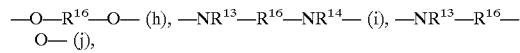

$R^{16}$ is selected from the group consisting of substituted or unsubstituted alkylene diradicals of 2 to 10 carbons, substituents being one or more lower alkyl radicals of 1 to 4 carbons, and arylene diradicals of 6 to 14 carbons, substituents being one or more lower alkyl radicals of 1 to 4 carbons.

2. A peroxide as defined in claim 1, selected from the group consisting of:
3-t-Butylperoxy-1,3-dimethylbutyl ethyl oxalate, 3-t-butylperoxy-1,3-dimethylbutyl chlorooxalate, di-(3-chlorocarbonylcarbonyloxy-1,1-dimethylbutyl) peroxide, 3-t-butylperoxy-1,3-dimethylbutyl hydrogen oxalate, allyl 3-t-butylperoxy-1,3-dimethylbutyl oxalate, N-t-butyl 3-t-butylperoxy-1,3-dimethylbutyl oxamate, 3-t-butylperoxy-1,3-dimethylbutyl 3-(neoheptanoylperoxy)-1,3-dimethylbutyl oxalate and OO-(1,1,3,3- tetramethylbutyl) O-(3-t-butylperoxy-1,3-dimethylbutyl) monoperoxyoxalate.

3. Peroxide composition as defined in claim 1 wherein R is a t-alkyl radical of 4 to 12 carbons.

4. Peroxide composition as defined in claim 1 wherein Z is Cl.

5. Peroxide composition as defined in claim 1 wherein Z is $OR^{13}$.

6. Peroxide composition as defined in claim 1 wherein Z is $NR^{13}R^{14}$.

7. Peroxide composition as defined in claim 1 wherein Z is OO—R.

8. Peroxide composition as defined in claim 1 wherein Z is $O-R^3-C(R^1)(R^2)-OO-R^{15}$.

9. A process for use of a peroxide composition as defined in claim 1 as a free-radical initiator, in effective initiating amounts, for the initiation of free-radical reactions selected from the group consisting of:

a. curing of unsaturated polyester resin compositions, b. polymerizing ethylenically unsaturated monomers compositions, c. crosslinking of olefin thermoplastic polymer compositions, d. curing of elastomer compositions, e. modifying polyolefin compositions, f. grafting of ethylenically unsaturated monomer substrates onto olefin homo- and copolymer substrates, and, g. compatibilizing blends of two or more normally incompatible polymer substrates;

which comprises heating said substrates in the presence of an effective initiating amount of one or more peroxides as defined in claim 1, for a time sufficient to at least partially decompose said peroxide, to perform the free-radical reaction.

* * * * *